United States Patent
Armstrong

(10) Patent No.: US 11,432,837 B2
(45) Date of Patent: Sep. 6, 2022

(54) MULTIFUNCTIONAL SURGICAL INSTRUMENT

(71) Applicant: Christopher Armstrong, Apopka, FL (US)

(72) Inventor: Christopher Armstrong, Apopka, FL (US)

(*) Notice: Subject to any disclaimer, the term of this patent is extended or adjusted under 35 U.S.C. 154(b) by 421 days.

(21) Appl. No.: 16/576,287

(22) Filed: Sep. 19, 2019

(65) Prior Publication Data

US 2020/0113591 A1 Apr. 16, 2020

Related U.S. Application Data

(60) Provisional application No. 62/901,599, filed on Sep. 17, 2019, provisional application No. 62/734,784, filed on Sep. 21, 2018.

(51) Int. Cl.
*A61B 17/29* (2006.01)

(52) U.S. Cl.
CPC .... *A61B 17/2909* (2013.01); *A61B 2017/291* (2013.01); *A61B 2017/2903* (2013.01); *A61B 2017/2926* (2013.01)

(58) Field of Classification Search
CPC . A61B 17/29; A61B 34/70; A61B 2017/0046; A61B 2017/00464; A61B 2017/2903; A61B 2017/291; A61B 2017/2923; A61B 2017/2926; A61B 17/2909
See application file for complete search history.

(56) References Cited

U.S. PATENT DOCUMENTS

| | | | |
|---|---|---|---|
| 9,993,258 B2 * | 6/2018 | Shelton, IV | A61B 17/1155 |
| 11,154,301 B2 * | 10/2021 | Beckman | A61B 17/115 |
| 2015/0238355 A1 * | 8/2015 | Vezzu | A61B 17/30 606/207 |
| 2016/0249927 A1 * | 9/2016 | Beckman | A61B 17/32002 227/177.1 |
| 2016/0249945 A1 * | 9/2016 | Shelton, IV | A61B 17/068 606/171 |
| 2019/0125384 A1 * | 5/2019 | Scheib | A61B 17/29 |
| 2019/0261991 A1 * | 8/2019 | Beckman | A61B 17/072 |
| 2020/0085436 A1 * | 3/2020 | Beckman | A61B 17/068 |
| 2021/0275176 A1 * | 9/2021 | Beckman | A61B 17/07207 |

* cited by examiner

*Primary Examiner* — George J Ulsh
(74) *Attorney, Agent, or Firm* — Jason T. Daniel, Esq.; Daniel Law Offices, P.A.

(57) ABSTRACT

A surgical instrument system includes a main body having a handle and a drive assembly. The drive assembly includes a plurality of gears and rotation transfer mechanisms for translating the movements of the handle into a mechanical force. A surgical tool having a tool body, an elongated shaft and an effector assembly is removably engaged to the main body of the system. The tool body houses a transfer gear assembly for engaging the drive assembly. A plurality of control wires extends from the transfer gear assembly to the effector assembly. The effector assembly includes a frame member having a pair of arms positioned along the distal end. The arms functioning to selectively open, close and move omnidirectionally based on an input of the handle.

16 Claims, 8 Drawing Sheets

MULTIFUNCTIONAL SURGICAL INSTRUMENT

CROSS-REFERENCE TO RELATED APPLICATIONS

This application claims the benefit of U.S. Application Ser. No. 62/734,784 filed on 21 Sep. 2018, and U.S. Application Ser. No. 62/901,599 filed on Sep. 17, 2019, the contents of each of which are incorporated herein by reference.

TECHNICAL FIELD

The present invention relates generally to surgical instruments, and more particularly to a multifunctional surgical instrument that can be customized and utilized for any number of different types of surgical procedures.

BACKGROUND

The statements in this section merely provide background information related to the present disclosure and may not constitute prior art.

Surgical instruments for performing medical surgery are well known in the art. Historically, medical surgeries have been performed using what is referred to as "open procedures." In an "open procedure," the surgeon typically makes a large incision in the vicinity of the operative site, performs the necessary procedure and then closes the wound. Typically, the wound is closed using sutures or other closing type devices, such as surgical staples. An example of an "open procedure" is the removal of the gall bladder.

In recent years we have seen the introduction and widespread use of micro-surgery using endoscopic techniques. These procedures are generally referred to as "minimally invasive surgery." The use of minimally invasive surgery has several attendant advantages, such as, for example, reduced medical costs, reduced hospital stays, and most importantly, reduced patient trauma. In this regard, many specialized surgical instruments and systems have been developed to facilitate minimally invasive surgeries. Of these instruments, the two main categories include handheld instruments and surgical robotic systems.

Handheld laparoscopic tools are by far the most common type of minimally invasive surgical instruments. These tools typically include an actuator that is positioned along one side of an elongated shaft for manipulating an effector that is positioned along the other side of the elongated shaft. Such handheld tools are relatively inexpensive and allow the surgeon to perform basic manipulations (e.g., open/close opposing jaws) using the tool, but do not allow for complex maneuvering and manipulations along 6 degrees of freedom, for example.

Conversely, there are many known robotic surgical systems that employ one or more remotely activated surgical arms having an effector along a distal end. These systems are typically operated by a surgeon who is located in a nearby console and allow the surgeon to manipulate the effector in a plurality of different range of motions. Although these systems provide greater freedom of movement for the instrument to function, they do not allow for haptic feedback in the manipulation of the tissues, are extremely expensive, and typically require the entire operating room the be reconfigured for use. As a result, these systems are not feasible for use in many field hospitals, third world countries and/or outlying hospitals.

Accordingly, it would be beneficial to provide a mechanical multifunctional surgical instrument system that combines the low cost and simplicity of a handheld laparoscopic tool with the increased functionality and full range of movement offered by a robotic system, without the drawbacks of each.

SUMMARY OF THE INVENTION

The present invention is directed to a surgical instrument system. One embodiment of the present invention can include a main body having a handle and a drive assembly. The drive assembly can include a plurality of gears and rotation transfer mechanisms for translating the movements of the handle into a mechanical force. A surgical tool having a tool body, an elongated shaft and an effector assembly can selectively engage the main body of the system.

In one embodiment, the tool body can house a transfer gear assembly for engaging the drive assembly. A plurality of control wires can be communicatively linked to the transfer gear assembly and terminate within the effector assembly.

In one embodiment, the effector assembly can include a frame member having a pair of arms positioned along the distal end. The arms being capable of selectively opening, closing and moving omnidirectionally based on an input of the handle.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

Figure 1:
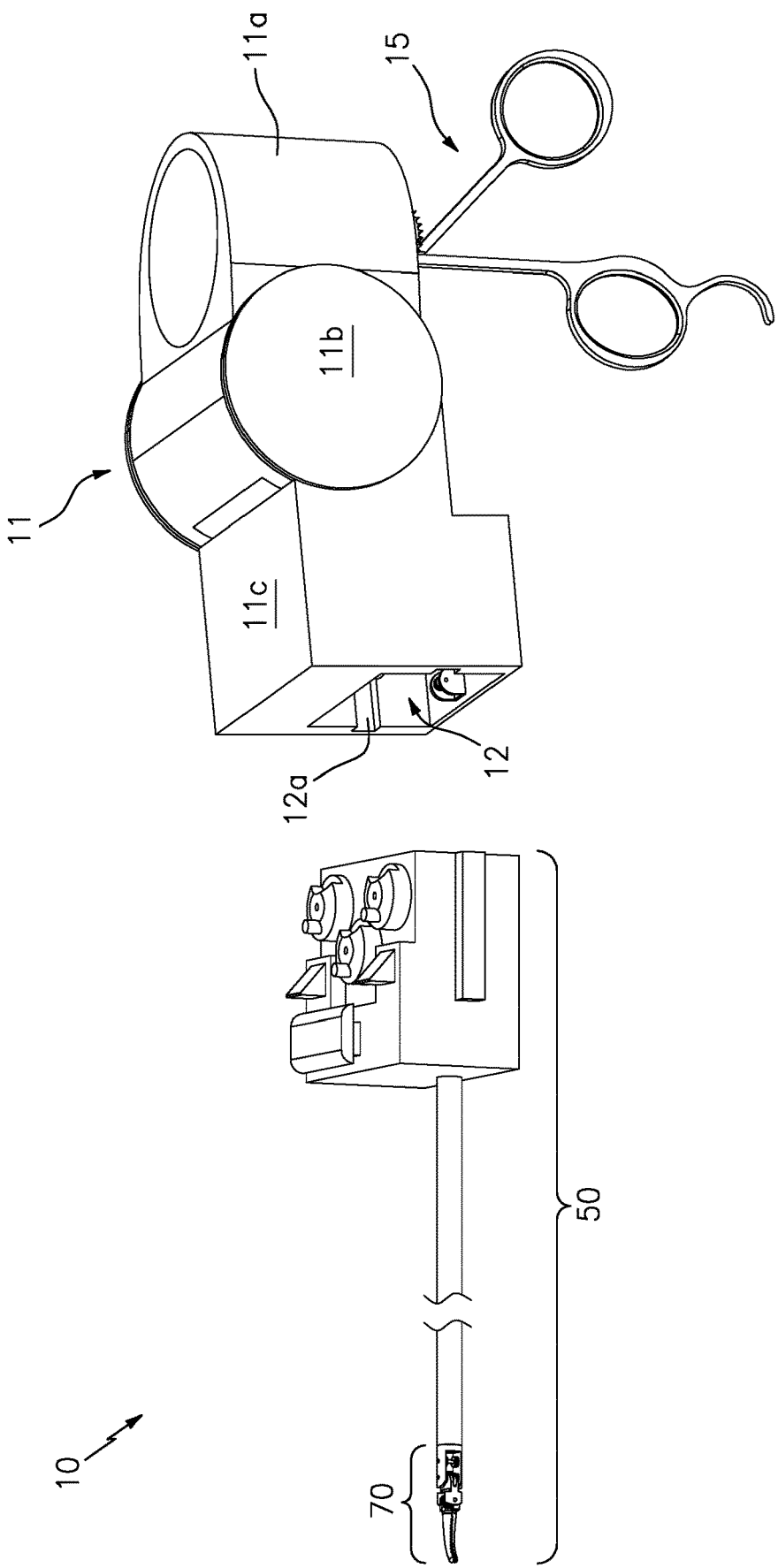
FIG. 1 is a perspective view of one embodiment of the multifunctional surgical instrument that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Definitions

As described herein, a "unit" or "assembly" means a series of specifically identified physical components or equivalent components that are linked together and/or function together to perform a specified function.

As described herein, the term "removably positioned," and derivatives thereof shall be used to describe a situation wherein two or more objects are joined together in a nonpermanent manner so as to allow the same objects to be repeatedly joined and separated.

As described herein, the terms "connector" and "complementary connector" include any number of different elements that work together to repeatedly join two items together in a nonpermanent manner. Several nonlimiting examples include opposing strips of hook and loop material (i.e. Velcro®), attractively-oriented magnetic elements or magnetic and metallic elements, flexible strips of interlocking projections with a slider (i.e., zipper), tethers, buckles such as side release buckles, and compression fittings such as T-handle rubber draw latches, hooks, snaps and buttons, for example. Each illustrated connector and complementary connector can be permanently secured to the illustrated portion of the device via a permanent sealer such as glue, adhesive tape, or stitching, for example.

As described throughout this document, the term "complementary shape," and "complementary dimension," shall be used to describe a shape and size of a component that is identical to, or substantially identical to the shape and size of another identified component within a tolerance such as, for example, manufacturing tolerances, measurement tolerances or the like.

FIGS. 1-8 illustrate one embodiment of a multifunctional surgical instrument system 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

As shown in FIG. 1, the system 10 can include, essentially, a main body 11 for positioning a handle 15 that is in operative communication with a drive assembly 200 (FIG. 2) positioned within the main body. The handle and drive assembly functioning to selectively manipulate an effector assembly 70 of an elongated removable tool 50.

As shown, the main body 11 can include a rear section 11a, a middle section 11b and a front section 11c. An aperture 12 can be positioned along the front section and can include indentations 12a for receiving a removable tool such as the tool 50 described below. Likewise, the handle can include a pair of handle segments 15a and 15b that can extend from the bottom surface of the main body and can be communicatively linked to the below described drive assembly 200.

Although described as including two distinct handle segments for manipulation of the effector, this is for illustrative purposes only. To this end, the handle 15 can include any number of different shapes, sizes, and number of components capable of receiving a user input to control an operation of the effector.

As described herein, the main body 11 may be formed from any number of different materials that can be joined together via known manufacturing techniques and that are, for example, relatively strong and stiff for their weight, while also being able to be repeatedly sanitized. Several nonlimiting examples include, but are not limited to various metals or metal alloys (e.g., aluminum, steel, titanium, or alloys thereof), plastic/polymers (e.g., high-density polyethylene (HDPE), rigid polyvinyl chloride (PVC), or polyethylene terephthalate (PET)), and/or various composite materials (e.g., carbon fibers in a polymer matrix, fiberglass, etc.). Although not specifically illustrated, the main body may also include a plurality of internal connectors for securely housing and positioning each of the device elements.

Figure 2:
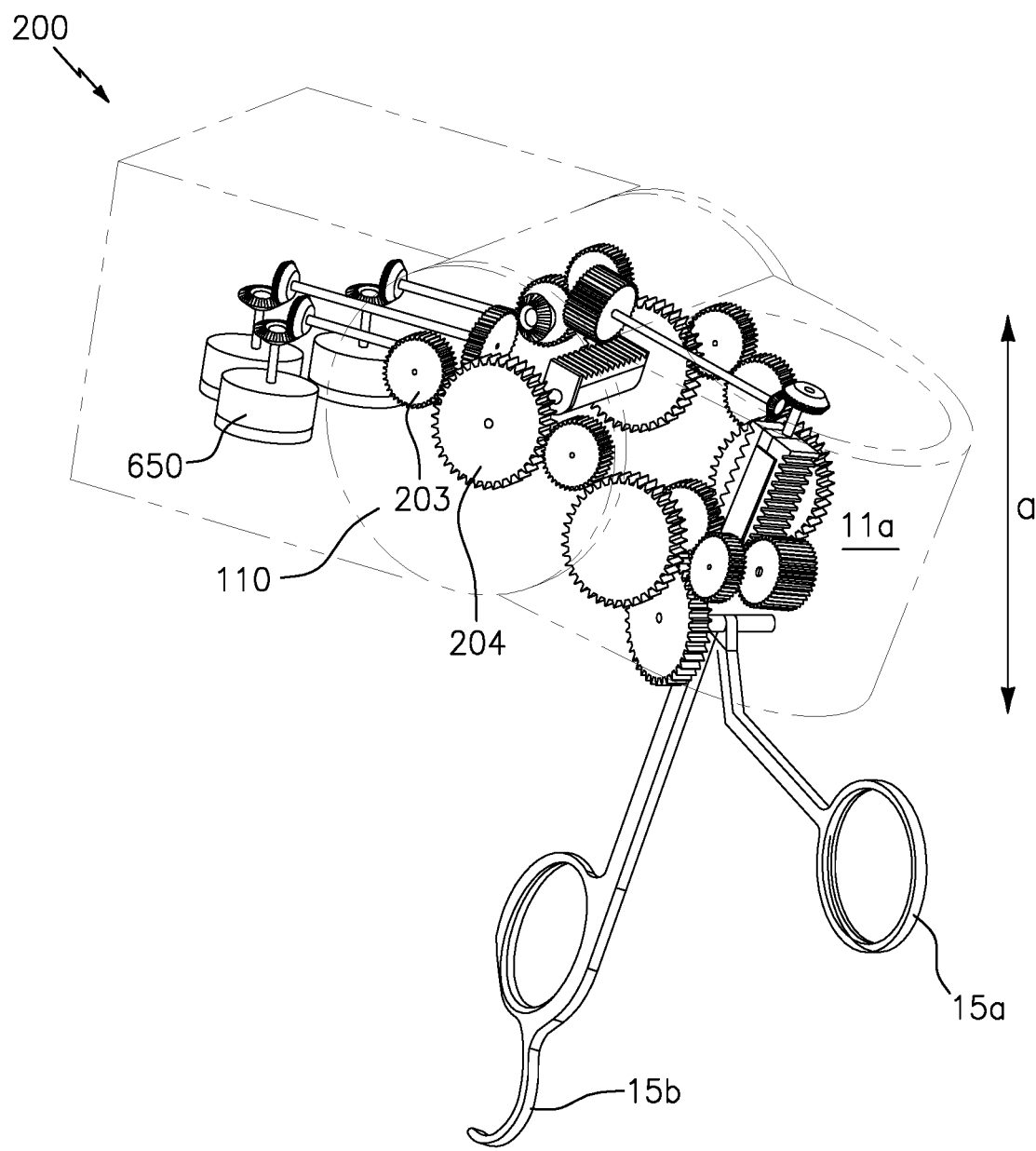
FIG. 2 is a perspective view of the main body of the multifunctional surgical instrument, in accordance with one embodiment of the invention.
Figure 3:
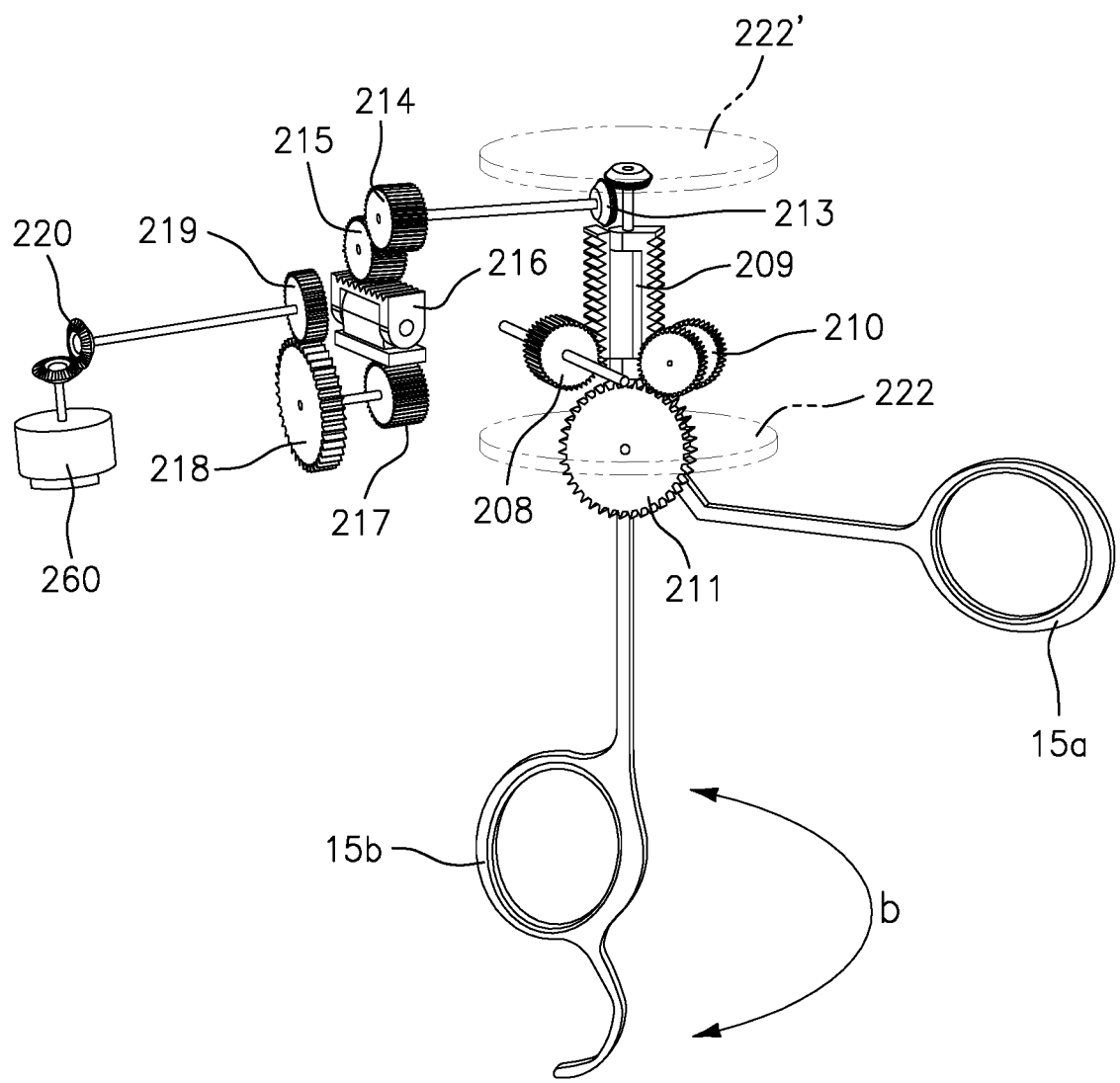
FIG. 3 is an exploded parts view of the drive assembly of the multifunctional surgical instrument, in accordance with one embodiment of the invention.
Figure 4:
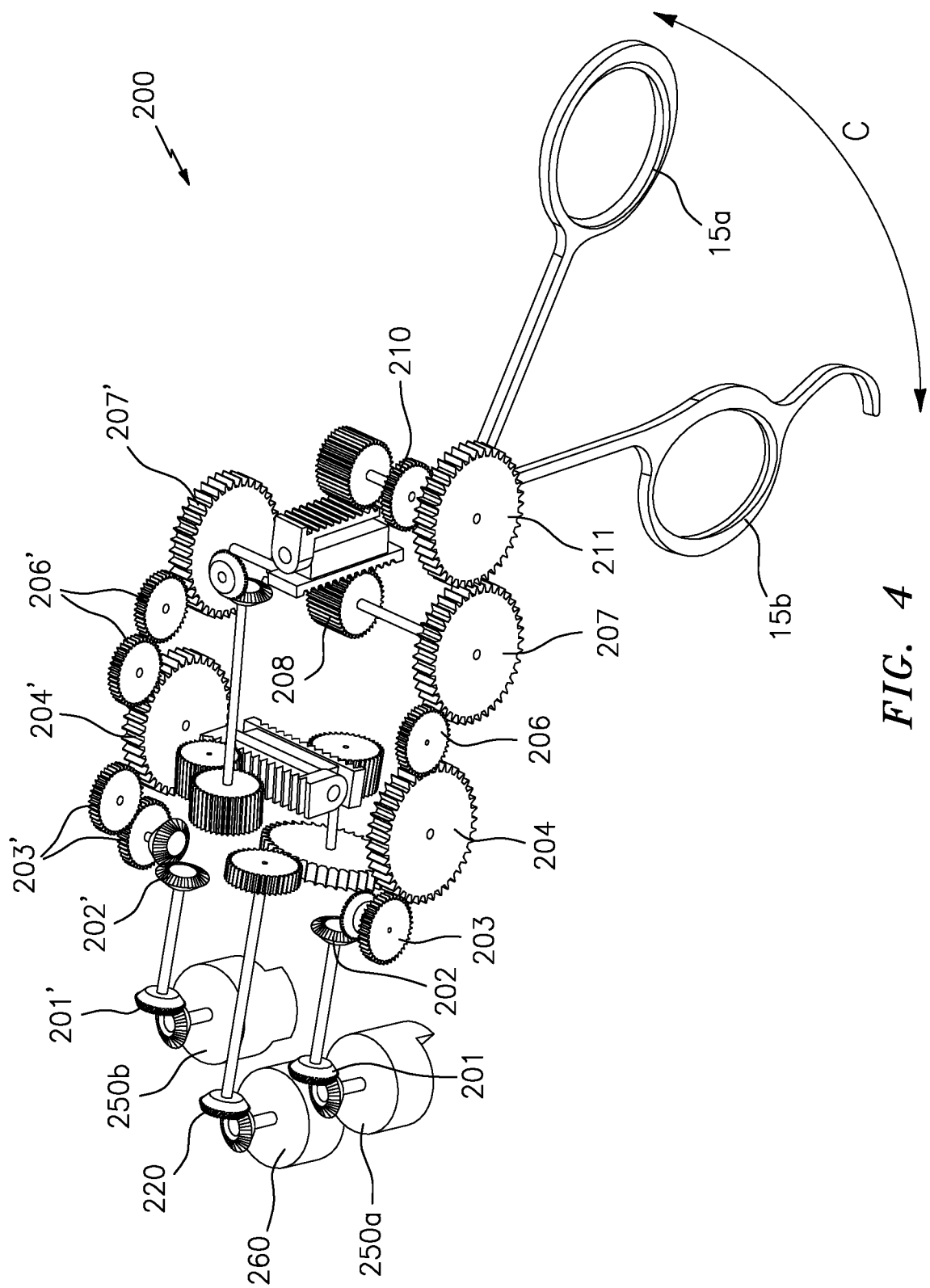
FIG. 4 is another exploded parts view of the drive assembly of the multifunctional surgical instrument, in accordance with one embodiment of the invention.

FIGS. 2-4 illustrate one embodiment of a drive assembly 200 which can be positioned within the main body 11. As shown the assembly 200 can include a plurality of gears that selectively manipulate three instrument wheels 250a, 250b, and 260 based on the movement of the handle segments 15a and 15b. As will be described below, the instrument wheels will be in communication with the removable tool so as to result in specified movement of the effector assembly 70.

As shown by arrow a in FIG. 2, the rear section 11a of the main body can move up and down based on the input of a device user. As the body 11a articulates through the vertical plane, gear 204 and middle body section 11b rotate relative to the rear section 11a. The rotation of gear 204 translates through additional gears 203, 202 and 201 onto instrument wheels 250a and/or 250b. In one embodiment, this vertical movement results in a corresponding change to the pitch of the effector 70, as shown by arrow a' in FIG. 8.

As shown by arrow b in FIG. 3, a twisting/horizontal rotation of handle segments 15a and 15b cause device body parts 222 and 222' to rotate in tandem about the plane relative to gear rack 209. Gear rack 209 is a two part fixture that allows translation and rotational change of direction simultaneously that is achieved by allowing the aft portion of the rack gear 209 to rotate with 222 and 222' while the forward portion of the rack gear 209 is not allowed to rotate because of resistance of gear 208. The rotational motion of 222' is transferred through a shaft to gear set 213 which changes the direction of rotation and transfers the rotation to gear 214.

Rack gear 216 changes the rotational motion of gear 215 to translational motion and is allowed to rotate about its center shafts axis just as at rack gear 209. This axial rotation is what allows the gear set continuity to be maintained while vertical articulation (as seen in FIGS. 2 and 4) is being performed. Gear 217 transfers the translation of rack gear 216 to rotational motion. The rotation is moved through gear 218 then gear 219 followed by gear set 220. Gear set 220 changes the direction of motion and allows rotation of the center instrument wheel 260. In one embodiment, this twisting motion causes a corresponding change to the yaw of the effector 70, as shown by arrow b' in FIG. 8.

As shown by arrow c in FIG. 4, articulation of handle segment 15a turns gear 211. which provides relative rotation through gear set 210. Gear set 210 causes gear rack 209 to translate through the vertical plane relative to 15a and causes rotation of gear 208. Gear 207 is connected to gear 208 by a shaft causing rotation of gear 207. Gear 207 transmits rotation to gear 204 through additional gears 206, 204, 203, 202 and 201 onto instrument wheel 250a. Likewise, parallel gears 207' 206',204',203',202' and 201' transmit rotation onto instrument wheel 250b. In one embodiment, this articulation causes the arms of the effector 70 to open and close, as shown by arrow c' in FIG. 8. In this regard, the two gears comprising 206' reverse the rotation relative to gear 206, thus cause the end effectors to rotate in opposite directions.

Figure 5:
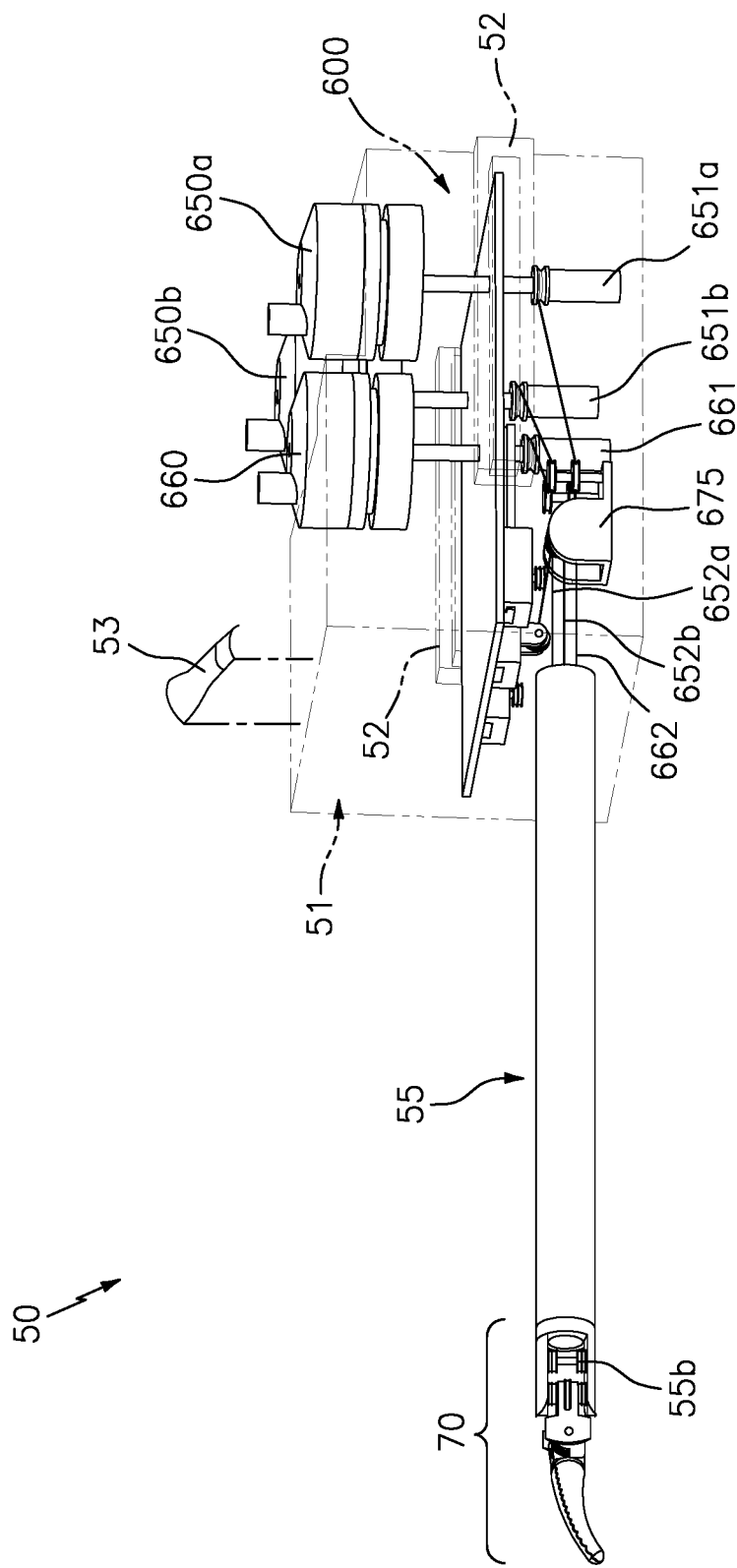
FIG. 5 is a perspective view of the removable tool of the multifunctional surgical instrument, in accordance with one embodiment of the invention.
Figure 6:
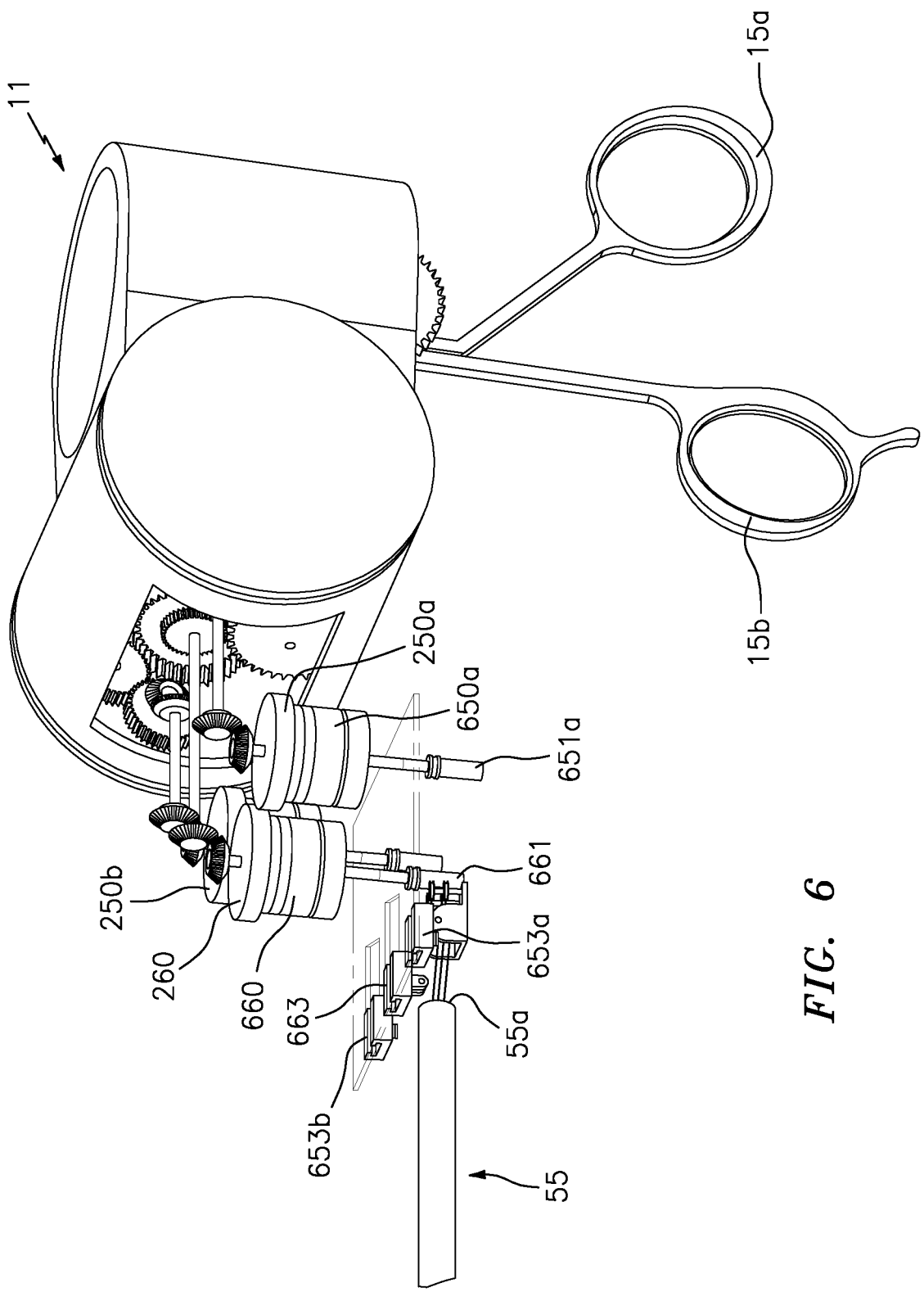
FIG. 6 is a cutout view of the drive assembly and the transfer gear assembly of the multifunctional surgical instrument, in accordance with one embodiment of the invention.

FIGS. 5 and 6 illustrate one embodiment of the removable tool 50, having a tool body 51 for housing a transfer gear assembly 600, an elongated shaft 55, and an effector 70 that is positioned along the distal end of the shaft.

As described herein, the tool body 51 can be constructed from the same materials or different materials as the main body 11. The tool body can include a pair of protrusions 52 along both sides, and a latching mechanism 53. The tool body 51 and protrusions 52 will preferably include a shape and size that are complementary to the shape and size of the aperture 12 and indentations 12a of the main body 11, respectively, so as to be removably positioned therein and secured by the latching mechanism 53. The latching mechanism can include any number of known connectors capable of removably securing the tool onto the main body.

The elongated shaft 55 can include an elongated generally hollow member having a first end 55a that is secured to the tool body 51 and a second end 55b that is secured to an effector 70. The shaft can be constructed to include any number of different lengths and diameters depending on the type of effector to be utilized and/or the intended use of the system. In either instance, the shaft will be constructed from a material suitable for insertion within a human body and can therefore comprise the same construction materials as the tool body 51, or a different material.

The transfer gear assembly 600 can be positioned within the tool body and can function to engage the instrument wheels 250a, 250b and 260 of the main body so as to provide a communicative instruction to the effector 70. As shown, rotation of the male instrument connectors 250a, 250b and 260 of the drive assembly 200 causes the female connectors 650a, 650b and 660 to rotate, thus causing rotation of wire sprockets 651a, 651b and 661 to which control wires 652a, 652b and 662 are attached. The wires then travel under tension to pulleys 653a, 653b and 663 respectively, then through the pulleys on the routing assembly 675, where they enter the first end 55a of the elongated shaft 55.

Figure 7A:
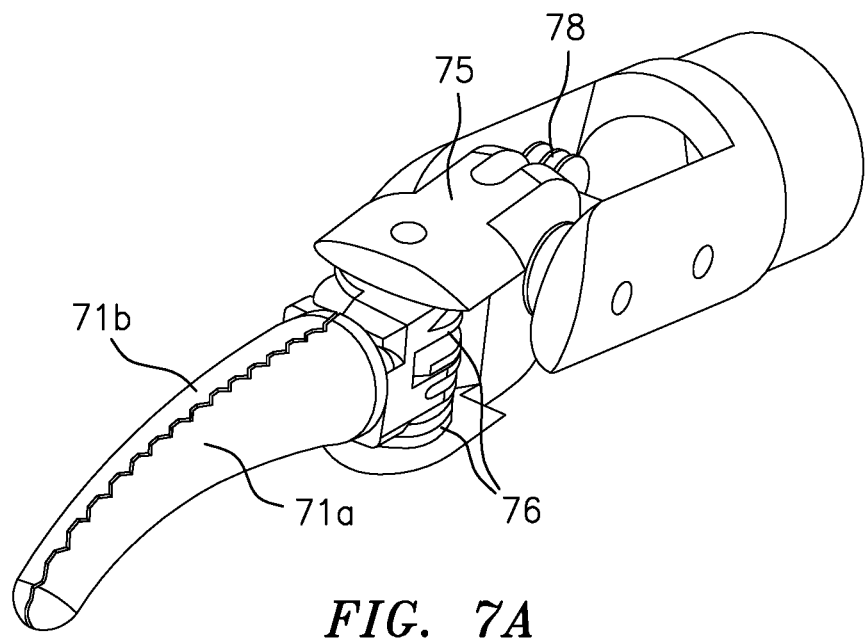
FIG. 7A is a perspective view of the effector assembly of the multifunctional surgical instrument, in accordance with one embodiment of the invention.
Figure 7B:
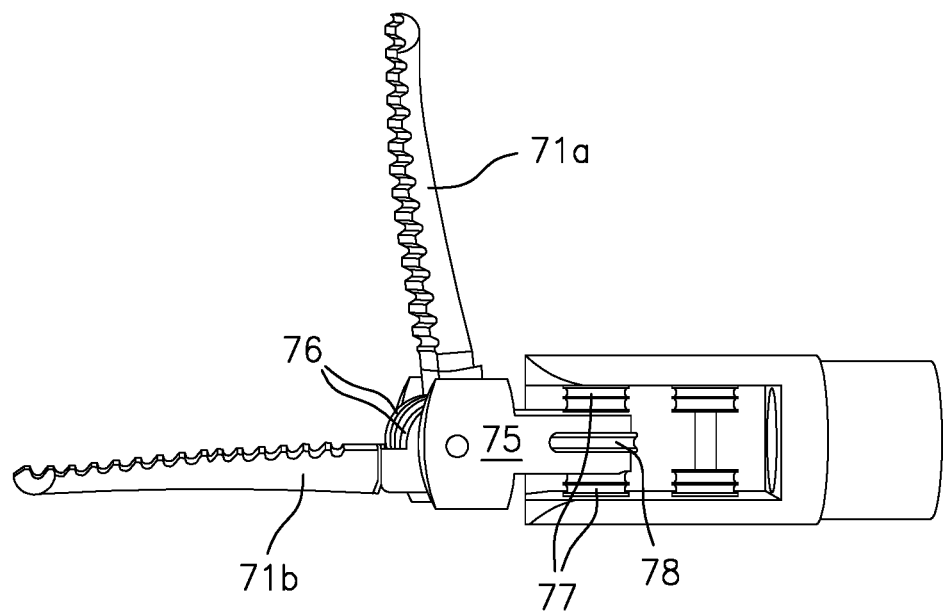
FIG. 7B is another perspective view of the effector assembly of the multifunctional surgical instrument, in accordance with one embodiment of the invention.

FIGS. 7A-7B illustrate one embodiment of an effector assembly 70 for use with the system 10. The effector can be constructed from the same material as the shaft 55 or a different material and can be communicatively linked to the transfer gear assembly 600 via the above described wires 652a, 652b and 662. In one embodiment, the assembly 70 can include a pair of arms 71a and 71b that are mounted onto a frame 75.

The rotation of arms 71a and 71b are directly related to pulleys 76 positioned within the frame and are supported by pulleys 77. The frame 75 can rotate on an axis at right angles relative to arms 71a and 71b in direct rotation to pulley 78. To this end, movement of handle segments 15a and 15b causes the gear assemblies 200 and 600 to selectively engage the control wires to move arm 71a, arm 71b and/or frame 75.

Figure 8:
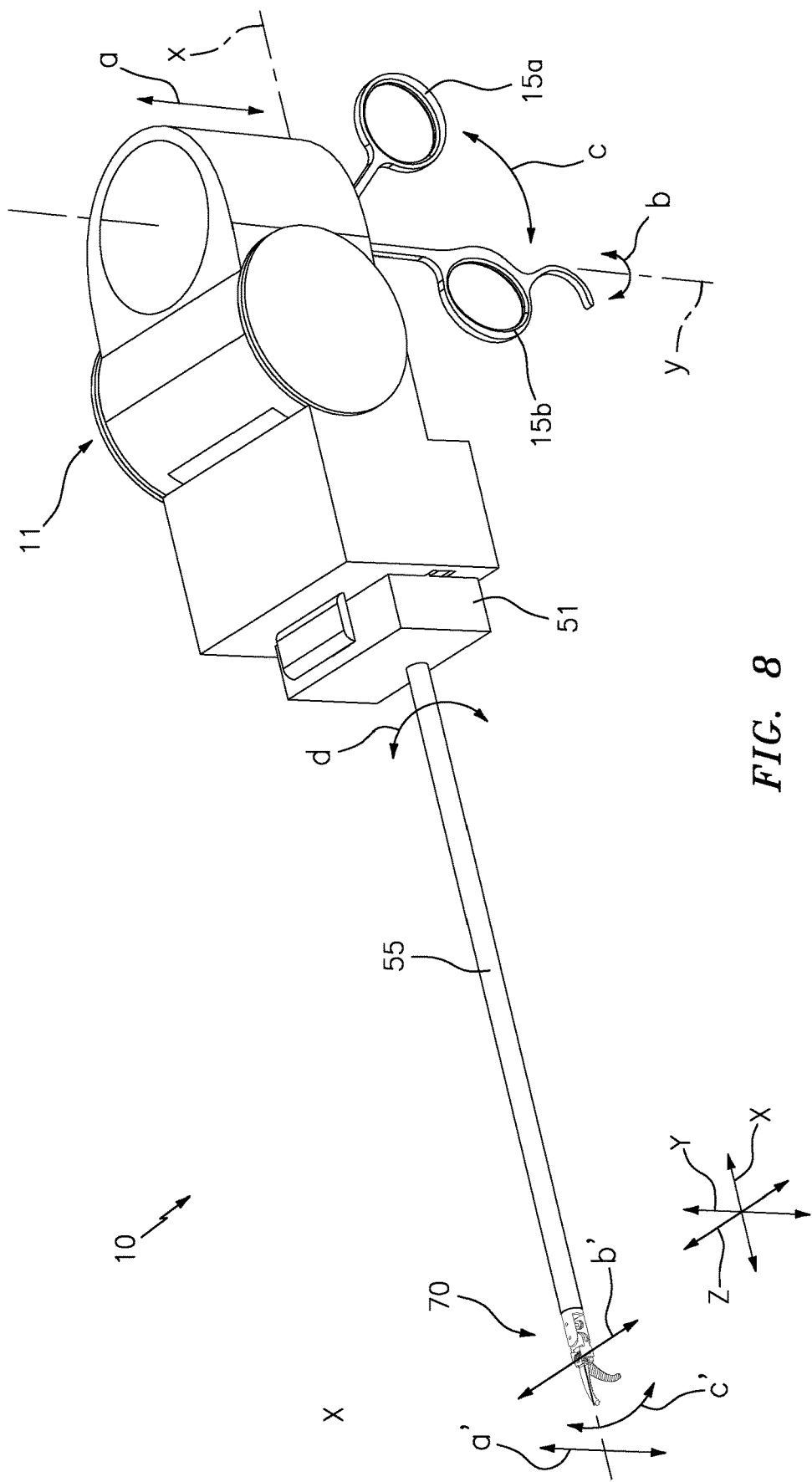
FIG. 8 is a perspective view of the multifunctional surgical instrument in operation, in accordance with one embodiment of the invention.

FIG. 8 illustrates one embodiment of the multifunctional surgical instrument system 10 in operation. As shown by arrow a, vertical movement of the handle segments 15a and 15b results in a corresponding vertical movement or "pitch" of the effector assembly 70 as shown by arrow a'. As shown by arrow b, a horizontal/twisting movement of the handle segments 15a and 15b results in a corresponding horizontal movement or "yaw" of the effector assembly 70 as shown by arrow b'

As shown by arrow c, rotation of the handle segments 15a and 15b about the vertical axis results in the separation and joining of the effector arms 71a and 71b, as shown by arrow c'. Finally, as shown by arrow d, the entire system 10 can be rotated left or right along the horizontal axis to change the "roll" of the effector assembly 70.

This combination of possible commands and resulting movements means that the effector is capable of achieving omnidirectional movement (e.g., 360-degree movement along and across both the horizontal X, vertical Y and Z axis), while also being able to open and close.

Although described above as including an effector assembly having a pair of grasping jaws, this is for illustrative purposes only. To this end, other embodiments are contemplated wherein different effector assemblies having different elements can be provided. Additionally, the system can be positioned onto or used in conjunction with any type of stand, sling or other mechanism to support the weight of the device during a surgical procedure.

Accordingly, the above described multifunctional surgical instrument system 10 advantageously offers the complete dexterity and freedom of movement of a surgical robot, while maintaining the low cost and ease of use typically associated with handheld surgical tools that is not rendered obvious by any of the known art.

As described herein, one or more elements of the system 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as additive manufacturing, welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the terms "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A surgical instrument system, comprising:
   a main body having a plurality of surfaces that define an interior space;
   a drive assembly that is positioned within the interior space;
   a handle that is in communication with the drive assembly and extends out of the main body; and
   a tool that includes,
   a tool body having a first end, a second end and an interior space,
   a transfer gear assembly that is positioned within the interior space of the tool body, said transfer gear assembly being configured to selectively engage the drive assembly,
   an elongated shaft having a first end that is in communication with the tool body, and a second end, and
   an effector assembly that is positioned along the second end of the elongated shaft, said effector assembly including a pair of movable arms that are configured to move omnidirectionally in response to a movement of the handle; and
   wherein the handle comprises two handle segments that extend outward from a major axis of the elongated shaft; and
   wherein a twisting/horizontal rotation of the two handle segments relative to the main body.

2. The system of claim 1, wherein the effector assembly comprises:
   a frame having a first end that is connected to the elongated shaft; and
   wherein the pair of movable arms are positioned along a second end of the frame.

3. The system of claim 2, wherein the arms are configured to selectively open and close in response to a movement of the handle.

4. The system of claim 1, wherein the tool is removably positioned onto the main body.

5. The system of claim 1, wherein the main body includes an opening along a front end.

6. The system of claim 5 wherein the tool body includes a shape and size that is complementary to the opening of the main body.

7. The system of claim 6, wherein the tool body is removably positioned within the opening of the main body.

8. The system of claim 1, wherein the tool body, the elongated shaft and the effector assembly are constructed from surgical grade steel.

9. The system of claim 1, wherein said move omnidirectionally includes each of a pitch movement of each of the pair of moveable arms, and a yaw movement of each of the pair of moveable arms.

10. The system of claim 1, wherein a first movement of the handle results in a corresponding pitch movement of the pair of moveable arms in a first direction.

11. The system of claim 10, wherein a second movement of the handle results in a corresponding pitch movement of the pair of moveable arms in a second direction.

12. The system of claim 11, wherein said first movement of the handle is opposite to said second movement of the handle, and said first direction is opposite to said second direction.

13. The system of claim 11, wherein a third movement of the handle results in a corresponding yaw movement of the pair of moveable arms in a third direction.

14. The system of claim 13, wherein a fourth movement of the handle results in a corresponding yaw movement of the pair of moveable arms in a fifth direction.

15. The system of claim 13, wherein said third movement of the handle is opposite to said fourth movement of the handle, and said fourth direction is opposite to said fifth direction.

16. The system of claim 1, wherein a portion of the main body is configured to move relative to another portion of the main body in response to the movement of the handle.

* * * * *